US006440979B1

(12) United States Patent
Cavalla et al.

(10) Patent No.: US 6,440,979 B1
(45) Date of Patent: Aug. 27, 2002

(54) ARYL ISOGUANINES

(75) Inventors: David Cavalla, Cambridge (GB); Peter Hofer, Liestal (CH); Mark Chasin, Manalapan, NJ (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/547,898

(22) Filed: Apr. 12, 2000

Related U.S. Application Data

(63) Continuation of application No. 08/860,680, filed as application No. PCT/US95/16723 on Dec. 12, 1995, now Pat. No. 6,066,641, which is a continuation-in-part of application No. 08/354,664, filed on Dec. 13, 1994, now abandoned.

(51) Int. Cl.[7] .................... C07D 473/22; C07D 473/04; C07D 401/04; A61K 31/522; A61P 11/06

(52) U.S. Cl. ........................ 514/261; 514/266; 544/276

(58) Field of Search ........................ 544/276; 514/261, 514/266

(56) References Cited

U.S. PATENT DOCUMENTS

| 4,710,503 A | 12/1987 | Hofer | .......................... | 514/263 |
| 4,925,847 A | 5/1990 | Hofer | .......................... | 514/263 |

FOREIGN PATENT DOCUMENTS

| EP | 0203721 | 12/1986 |
| EP | 0386675 | 9/1990 |
| EP | 0415456 | 3/1991 |
| EP | 0417790 | 3/1991 |
| EP | 423805 | 4/1991 |
| EP | 0435811 | 7/1991 |
| WO | 9500516 | 1/1995 |

OTHER PUBLICATIONS

"s–Triazole (3,4–i)Purine Derivative", Patent Abstracts of Japan #03–204879, Sep. 6, 1991.
"Condensed Purine Derivative", Patent Abstracts of Japan #03–204880, Sep. 6, 1991.
K.A. Jacobson, et al., "Sulfur–Containing 1,3–Dialkylxanthine Derivatives as Selective Antagonists at A1–Adenosine Receptors," *J. Med. Chem.* (1989), 32, 1873–1879.
A.K. Armitage, et al., "Structure–Activity Relationships in a Series of 6–Thioxanthines with Bronchodilator and Coronary Dilator Properties," *Brit. J. Pharmacol.* (1961), 17, 196–207.
Chem Abstracts 12th Collective Chemical Substance Index, p. 77818 (undated).

*Primary Examiner*—Mark L Berch
(74) *Attorney, Agent, or Firm*—Davidson, Davidson & Kappel, LLC

(57) ABSTRACT

Disclosed are compounds having formula (II):

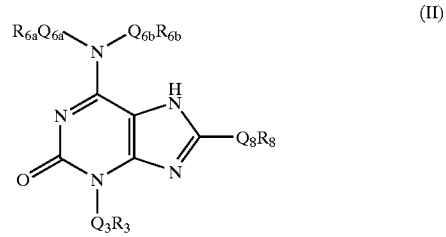

wherein: $Q_3$, $Q_{6a}$, $Q_{6b}$ and $Q_8$ are independently a bond, $C_{1-8}$ alkylene, $C_{2-8}$ alkenylene and $C_{2-8}$ alkynylene, and $R_3$, $R_{6a}$, $R_{6b}$ and $R_8$ are independently hydrogen, aryl or heteroaryl, optionally substituted by halogen, hydroxy, alkoxy, nitro, cyano and carboxy, provided that: $Q_3R_3$ is not hydrogen or methyl. The compounds are effective PDE IV inhibitors and possess improved PDE IV inhibition and improved selectivity with regard to PDE III inhibition.

16 Claims, No Drawings

ARYL ISOGUANINES

This application is a continuation of U.S. patent application Ser. No. 08/860,680 U.S. Pat. No. 6,066,641 filed Jun. 11, 1997 which is a 35 U.S.C §371 filing of International Application No. PCT/US95/16723 which was filed on Dec. 12, 1995 which is a continuation-in-part of U.S. patent application Ser. No. 08/354,664, filed on Dec. 13, 1994, now abandoned the disclosures of which are herein incorporated by reference.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to stem also from its anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these actually may contribute to its activity, only PDE inhibition may account for both the anti-inflammatory and bronchodilatory components. however, theophylline is known to have a narrow therapeutic index, and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is CAMP specific, and its inhibition causes airway relaxation, anti-inflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula:

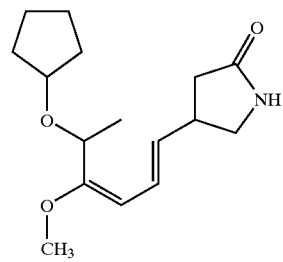

and of Ro-20-1724, which has the following structural formula:

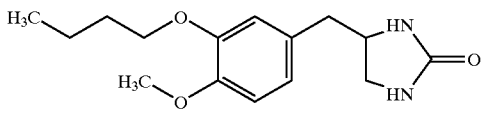

have been studied.

Rolipram, which was initially studied because of its activity as an antidepressant has been shown to selectively inhibit the PDE IV enzyme and this compound has since become a standard agent in the classification of PDE enzyme subtypes. There appears to be considerable therapeutic potential for PDE IV inhibitors. Besides initial work suggesting an anti-depressive action, rolipram has been investigated for its anti-inflammatory effects, particularly in asthma. In-vitro, rolipram, Ro-20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and anti-inflammatory properties would be most advantageous.

It appears that selective PDE IV inhibitors should be more effective with fewer side effects than theophylline.

Attempts have therefore been made to find new compounds having more selective and improved PDE IV inhibition.

OBJECTS AND SUMMARY OF THE INVENTION

It is accordingly a primary object of the present invention to provide new compounds which are effective PDE IV inhibitors.

It is another object of the present invention to provide new compounds which act as effective PDE IV inhibitors with lower PDE III inhibition.

It is a further object of the present invention to provide new compounds which have a substantially equal or superior PDE IV inhibitory effect as compared to theophylline or other known chemical compounds, and which exhibit surprisingly greater selectivity with regard to their PDE inhibitory effects.

It is another object of the present invention to provide a method of treating a patient requiring PDE IV inhibition.

It is another object of the present invention to provide new compounds for treating disease states associated with abnormally high physiological levels of cytokines, including tumor necrosis factor.

It is another object of the present invention to provide a method of synthesizing the new compounds of this invention.

It is another object of the present invention to provide a method for treating a mammal suffering from a disease state selected from the group consisting of asthma, allergies, inflammation, depression, dementia, a disease caused by Human Immunodeficiency Virus and disease states associated with abnormally high physiological levels of cytokines.

With the above and other objects in view, the present invention mainly comprises compounds of the formulae:

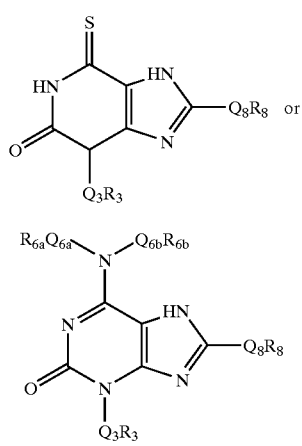

wherein:

$Q_3$, $Q_{6a}$, $Q_{6b}$ and $Q_8$ are independently a bond, $C_{1-8}$ alkylene, $C_{2-8}$ alkenylene and $C_{2-8}$ alkynylene, and $R_3$, $R_{6a}$, $R_{6b}$ and $R_8$ are independently hydrogen, aryl or heteroaryl, optionally substituted by halogen, hydroxy, alkoxy, nitro, cyano and carboxy, provided that:

$Q_3R_3$ is not hydrogen or methyl in formulae (I) or (II); and at least one of $R_3$ and $R_8$ is aryl or heteroaryl in formula (I).

The alkylene, alkenylene and alkynylene moieties can be straight or branched, and/or be optionally substituted with an aryl.

When at least one of $R_3$, $R_{6a}$, $R_{6b}$, and $R_8$ is aryl, it is preferably phenyl or naphthyl; when at least one of $R_3$, $R_{6a}$, $R_{6b}$, and $R_8$ is heteroaryl, it is preferably pyridyl, pyrimidyl, quinolyl or isoquinolyl.

In other aspects of the invention, pharmaceutical compositions and methods of treating mammals suffering from disease states such as asthma, allergies, inflammation, depression, dementia, atopic diseases, rhinitis and the like are provided.

DETAILED DESCRIPTION

The compounds of the present invention, as demonstrated in the appended examples, are effective in the mediation or inhibition of PDE IV in humans and other mammals. Further, these compounds are selective PDE IV inhibitors which possess both bronchodilatory and anti-inflammatory properties substantially without undesirable cardiovascular stimulation caused by PDE III inhibition. Many of these compounds have a substantially equal or superior PDE IV. inhibitory effect as compared to theophylline.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

The compounds of the present invention comprise the formulae:

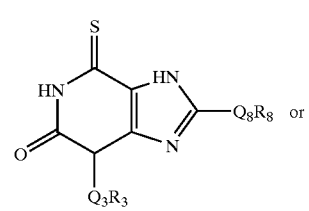

-continued

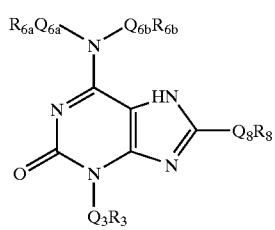

(II)

wherein:
$Q_3$, $Q_{6a}$, $Q_{6b}$, and $Q_8$ are independently a bond, $C_{1-8}$ alkylene, $C_{2-8}$ alkenylene and $C_{2-8}$ alkynylene; and
$R_3$, $R_{6a}$, $R_{6b}$ and $R_8$ are independently hydrogen, aryl or heteroaryl, optionally substituted by halogen, hydroxy, alkoxy, nitro, cyano and carboxy, provided that:
$Q_3R_3$ is not hydrogen or methyl in formulae (I) or (II); and at least one of $R_3$ and $R_8$ is aryl or heteroaryl in formula (I).

The $C_{1-8}$ alkylene, $C_{2-8}$ alkenylene and $C_{2-8}$ alkynylene moieties can be straight, branched and/or substituted with an aryl. That is, they can be aralkyl, aralkenyl, or aralkynl groups. Preferable aralkyl moieties include phenalkyl, naphthalkyl and heteroaralkyl.

The alkyl portion of the aralkyl moieties is preferably a lower alkyl. The term "lower" is defined for purposes of the present invention as straight or branched chain radicals having from 1 to 3 carbon atoms. When aralkenyl, or aralkynyl embodiments are included, suitable aralkenyl moieties include ethenyl and suitable aralkynyl groups include ethynyl.

The compounds of the present invention are preferably 6-thioxanthines or isoguanine derivatives. One of $R_3$, $R_{6a}$, $R_{6b}$, and $R_8$ may be an aryl or a heteroaryl. In this regard, suitable aryl moieties include phenyl and naphthyl. Suitable heteroaryl moieties include pyridyl, pyrimidyl, quinolyl and isoquinolyl.

For example, the compounds of the invention can include phenyl moieties substituted with one or two alkoxy groups, or a halogen, with chlorine being particularly preferred. Some particularly preferred heteroaralkyls include pyridyls.

Although both $R_3$ and $R_8$ can be aryl or aralkyl moieties, in most embodiments, however, at most only one of $R_3$ and $R_8$ is such. Therefore, as an alternative to the aryl and aralkyl moieties set forth above, $R_3$ and $R_8$ can also be hydrogen, such that $Q_3R_3$ or $Q_8R_8$ can be a $C_{1-9}$ alkyl which can be branched or unbranched, unsubstituted or substituted with one or more halogens, hydroxy or alkoxy groups, or cycloalkyl groups.

Particularly preferred, however, are hydrogen, methyl, ethyl, propyl, isopropyl and cyclopropyl.

Within the formula set forth above, the following compounds are particularly preferred:
3-(3-cyclopentyloxy-4-methoxybenzyl)-8-isopropyl-6-thio-xanthine;
3-(4-chlorobenzyl)-6-thio-xanthine;
8-isopropyl-3-(4-pyridylmethyl)-6-thio-xanthine;
3-(3-chlorobenzyl)-8-isopropyl-6-thio-xanthine;
3-(4-chlorobenzyl)-$N^6$-ethyl-8-isopropyl-isoguanine;
3-(cyclopropylmethyl)-8-(1-methyl-ethyl)-$N^6$-propyl-isoguanine hydrochloride;
8-cyclopropyl-3, $N^6$-diethyl-isoguanine hydrochloride;
3-(3-cyclopentyloxy-4-methoxybenzyl)-6-thio-xanthine;
3-(4-chlorophenyl)-8-isopropyl-6-thio-xanthine;
8-(3-cyclopentyloxy-4-methoxybenzyl)-3-ethyl-6-thio-xanthine;
8-(3,4-dimethoxybenzyl)-3-propyl-6-thio-xanthine; and
8-(2-naphthylmethyl)-3-propyl-6-thio-xanthine.

Description of the syntheses of these molecules is set forth in the Examples. The syntheses of other molecules not specifically shown in the examples but within the scope of the invention are carried out using those techniques shown with modifications which are known to those of ordinary skill in the art.

The compounds of the present invention have been found to be highly effective PDE IV inhibitors, the inhibition of which is in fact significantly and surprisingly greater than that of theophylline which exhibits 50% inhibition of PDE IV at around 350 $\mu$M.

Thus, the concentration which yields 50% inhibition of PDE IV ($IC_{50}$) for the compound prepared in Example 1 is 1.0 $\mu$M, whereas the $IC_{50}$ for rolipram when run in the same assay was 2.8 $\mu$M. It is apparent that this inventive compound is several times as effective as a PDE IV inhibitor as compared to rolipram (or theophylline).

While the $IC_{50}$ for PDE III inhibition of an Example 1 compound is approximately 25 $\mu$M, it is nonetheless clear that it and the other compounds of the invention are highly selective PDE IV inhibitors.

Accordingly, the compounds of the present invention can be administered to anyone requiring PDE IV inhibition. Administration may be orally, topically, by suppository, inhalation or insufflation, or parenterally.

The present invention also encompasses, where appropriate, all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating oh the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

Various compounds of the present invention are also potent PDE V inhibitors, which reduce smooth muscle cell proliferation and increase pulmonary vasodilation. A combination of of PDE IV and V inhibition is believed to be of benefit in certain medical conditions, such as for inhibition of e.g. restenosis and related diseases.

The PDE IV inhibitory compounds of the present invention may be examined for their PDE IV inhibitory effects via the techniques set forth in the following examples, wherein the ability of the compounds to inhibit PDE IV isolated from bovine tracheal smooth muscle is set forth.

DESCRIPTION OF THE PREFERRED EMBODIMENTS

The following examples illustrate various aspects of the present invention, and are not to be construed to limit the claims in any manner whatsoever.

EXAMPLE 1

3-(3-Cyclopentyloxy-4-methoxy-benzyl)-8-isopropyl-6-thioxanthine a) 3-Cyclopentyloxy-4-methozy-benzyl Urea 25 ml of 5N HCl was added to a solution of 31.54 g of 3-cyclopentyloxy-4-methoxy-benzylamine carbonate and 8.30 g of sodium cyanate in 440 ml of water and 50 ml of THF over 15 minutes. After 3 hours another 0.83 g of sodium cyanate was added. After 20 hours the solid was collected, washed with water containing 5% of THF, suspended in 2.2 liters of ether and collected to give the title compound as a white solid (28.55 g) mp 134–5° C.

b) 1-Cyanoacetyl-3-(3-cyclopentyloxy-4-methoxy-benzyl) Urea 9.64 g of 98% cyanoacetic acid and 38 ml of acetic anhydride were heated for 1 hour at 65° C. A fine suspension of 27.93 g of 3-cyclopentyloxy-4-methoxy-benzyl urea in 280 ml of THF was added. After 4 hours at 65° C. the THF was distilled off, the residue diluted with 150 ml of toluene and the solid collected at 5° C., to give the title compound as a white solid (25.44 g). The filtrate was evaporate to dryness, the residue suspended in toluene and further title compound (4.89 g) collected.

c) 6-Amino-1-(3-cyclopentyl-4-methoxy-benzyl)-uracil

A suspension of 30.33 g of 1-cyanoacetyl-3-(3-cyclopentyloxy-4-methoxy-benzyl) urea in 200 ml of 2-propanol was added to a solution of 1.28 g of potassium hydroxide in 67 ml of 2-propanol and heated under reflux for 1 hour. After an initial dissolution a precipitate was formed. The solid was collected at 5° C. and washed to give 21.10 g of crude title compound. The filtrate was evaporated to dryness, treated with 100 ml of water and a little diethyl ether and acidified to pH 6. The crystals were collected, suspended in hot methanol and collected at 5° C. to give 4.66 g of additional product.

d) 6-Amino-1-(3- cyclopentyloxy-4-methoxy-benzyl-5-nitroso-uracil 15.81 ml of 4N sodium nitrite solution was added dropwise at 65°–70° C. over 8 minutes to a solution of 20.53 g of 1-(3-cyclopentyloxy-4-methoxy-benzyl) 6-amino uracil in 300 ml of acetic acid. After 30 minutes the suspension was cooled to room temperature and the solid collected and washed with water to give the title compound (19.36 g) as pink crystals. The filtrate was evaporated to dryness, the residue suspended in 100 ml of water and the solid collected to give 1.98 g as a second crop.

e) 6-Amino-1-(3-cyclopentyloxy-4-methoxy-benzyl)-5-isobutyrylamino-uracil 4.32 g of 6-amino-1-(3-cyclopentyloxy-4-methoxy-benzyl)-5-nitroso-uracil, 2.00 g of sodium bicarbonate and 2.98 ml of isobutyric anhydride in 80 ml of DMF were hydrogenated with 1.68 g of neutral Raney-nickel at room temperature. After 9 hours the mixture was heated for 15 minutes to 60° C. The nickel was filtered off, the filtrate evaporated to dryness and the residue suspended in 100 ml of water. At pH 8 the solid was collected to give the crude title compound (4.64 g) as a white solid.

f) 3-(3-Cyclopentyloxy-4-methoxy-benzyl)-8-isopropyl-xanthine

A mixture of 4.64 g of 6-amino-1-(3-cyclopentyloxy-4-methoxy-benzyl)-5-isobutyrylamino-uracil, 100 ml of water and 50 ml of 1N NaOH was heated under reflux for 1 hour. The solution was filtered, treated with 0.25 g of charcoal, filtered again and neutralized to pH 8. The solid was collected, dried, and recrystallized from THF to give the title compound (4.03 g) as a white solid mp 282–3° C.

g) 3-(3-Cyclopentyloxy-4-methoxy-benzyl)-8-isopropyl-6-thioxanthine 3.59 g of 3-(3-cyclopentyloxy-4-methoxy-benzyl)-8-isopropyl-xanthine and 2.40 g of phosphorus pentasulfide were heated under reflux in 60 ml of pyridine for 8 hours. At –5° C., 11.9 ml of 2N NaOH were added slowly. The suspension was evaporated to dryness, the residue suspended in 100 ml of water, neutralized to pH 8, and the solid, collected, washed and dried to give the crude 6-thioxanthine (3.45 g). Purification by filtration chromatography (SiO$_2$, 15g; chloroform) yielded a solid which was reprecipitated from NaOH by addition of HCl, to pH 6.5, collected, washed and dried to give the monohydrate of the title compound (3.38 g) as a white solid, mp 192–3° C.

Elemental analysis for $C_{21}H_{20}N_4O_4S \cdot H_2O$; % calc.: C 58.31, H 6.52, N 12.95, O 14.80%; % found: C 58.60, H 6.36, N 12.91, O 15.06%.

EXAMPLE 2

3-(4-Chlorobenzyl)-6-thioxanthine a) 4-Chlorobenzylurea 100 ml of 95% 4-chlorobenzylamine and 51.53 g of sodium cyanate in 1 liter of water were treated below 25° C. with 194 ml of 4N HCl. Further sodium cyanate (5.15 g) was added and the pH adjusted to 7.3. After 3 days the solid was collected, washed with water and dried to give the title compound (131.1 g) as a white solid mp 186–9° C.

b) 1-(4-Chlorobenzyl)-3-cyanoacetyl-urea 68.7 g of 98% cyanoacetic acid and 155 ml of acetic anhydride were kept at 65° C. for 30 minutes. 4-chlorobenzylurea (132.9 g) was added in portions over 10 minutes. After 2 hrs. at 70–75° C., further acetic anhydride (25 ml) was added. After a further 15 minutes, 90 ml of toluene was added, cooled to room temperature, the solid collected and washed with toluene to give the title compound (155.60 g) as a white-solid mp 203–6° C.

c) 6-Amino-1-(4-chlorobenzyl)-uracil 155.6 g of 1-(4-chlorobenzyl)-3-cyanoacetyl-urea in 230 ml of 2-propanol were added to a solution of 14.0 g of KOH in 450 ml of 2-propanol and heated under reflux for 1 hour. After cooling the solid was collected and washed to give the title compound (153.4 g) as a white solid mp 238–41° C.

d) 6-Amino-1-(4-chlorobenzyl)-5-nitroso-uracil 157.6 ml of 4N sodium nitrite was added over 45 minutes to a suspension of 165 g of 6-amino-1-(4-chlorobenzyl)-uracil in 825 ml of acetic acid at 65–70° C. After a further 15 minutes at 70° C. the reaction mixture was cooled to room temperature, the pink solid collected and washed with 80% acetic acid and water to give the title compound (150.9 g) mp >320° C.

e) 6-Amino-1-(4-chlorobenzyl)-5-formylamino-uracil 150.0 g of 6-amino-1-(4-chlorobenzyl)-5-nitroso-uracil were dissolved in 1.2 liters of formic acid at 70° C. and treated over 1.5 hours in portions with 76.84 g of zinc powder keeping the temperature between 75–80° C. After cooling to 55° C. the solid was filtered of, the residue resuspended in 800 ml of formic acid and the solid again filtered off. The filtrates were evaporated to a solid which was suspended in 350 ml of water. The solid was collected, washed and dried to give the title compound (149.1 g) as a white solid, mp 274–8° C.

f) 3-(4-Chlorobenzyl-xanthine

6-Amino-1-(4-chlorobenzyl)-5-formylamino-uracil (25.58 g) in 200 ml of 2N NaOH and 150 ml of water was heated under reflux for 3 hours. Charcoal (2.6 g) was added, and after filtration the solution was neutralized to pH 7.0 and the solid collected. Reprecipitation from NaOH by neutralization with HCl gave 22.91 g of title compound as a white solid mp 304–10° C.

g) 3-(4-Chlorobenzyl)-6-thioxanthine 11.06 g of 3-(4-chlorobenzyl)-xanthine and 11.34 g of phosphorus pentasulfide were heated under reflux in 112 ml of pyridine for 4 hours. After cooling to 10° C., 52 ml of 2N NaOH were added over 30 minutes. The mixture was evaporated to dryness, the residue suspended in 120 ml of water and the pH adjusted to 7.5. The solid was collected, redissolved in 150 ml of 1N NaOH, treated with 0.6 g of charcoal, filtered and neutralized to pH 7.0. The solid was collected again to give the title compound (10.07 g) mp 313–7° C.;

Elemental analysis for $C_{12}H_9ClN_4OS$; % calc.: C 49.23, H 3.10, N 19.14, S 10.95%; % found: C 49.05, H 2.93, N 19.00, S 11.28%.

EXAMPLE 3

8-Isopropyl-3-(4-picolyl)-6-thioxanthine a) 4-Picolylurea 5.1 ml of 5N HCl was added to a solution of 2.53 ml of 4-picolylamine and 1.66 g of sodium cyanate in 50 ml of water. After 5 hours, a further 0.166 g of cyanate were added and the pH adjusted to 7.5. After 18 hours the reaction mixture was evaporated to dryness, the residue extracted with 100 ml of hot 2-propanol. The filtrate was concentrated, cooled and the solid collected to give the title compound (3.03 g) mp 194–6° C. A further 0.63 g could be isolated as second and third crops.

b) 1-Cyanoacetyl-3-(4-picolyl)-urea 2.20 g of cyanoacetic acid and 8.7 ml of acetic anhydride were kept for 1 hour at 65° C., 3.65 g of 4-picolylurea suspended in 27 ml of THF were added. After 2 hours at 65° C. the mixture was cooled the solid collected and washed with THF to give the title compound (3.84 g) as a white solid mp 193–5° C.

c) 6-Amino-1-(4-picolyl)-uracil 3.91 g of 1-cyanoacetyl-3-(4-picolyl)-urea were added at 60° C. to a solution of 0.24 g of KOH in 40 ml of 2-propanol. After 1.5 hours at reflux the mixture was cooled, the solid was collected, washed and dried to give the crude title compound (2.98 g) mp 163–8° C.

d) 6-Amino-5-nitroso-1-(4-picolyl)-uracil 2.6 ml of 4N sodium nitrite was added to a solution of 2.35 g of 6-amino-1-(4-picolyl)-uracil in 25 ml of water and 4 ml of 5N HCl. After 15 minutes, 10 ml of 1N sodium bicarbonate was added. The solid was collected, washed and dried to give the title compound (2.15 g).

e) 8-Isopropyl-3-(4-picolyl)-xanthine 2.07 g of 6-amino-5-nitroso-1-(4-picolyl)-uracil, (1.34 g) of sodium bicarbonate and 2.0 ml of isobutyric anhydride in 40 ml of DMF were hydrogenated with 0.83 g of neutral Raney-nickel at room temperature. After 2 hours the hydrogenation was completed, and kept for 15 minutes at 60° C. The nickel was filtered off and the filtrate evaporated to dryness. The residue was heated under reflux in 40 ml of 1N NaOH and 150 ml of water for 20 minutes, 0.2 g of charcoal was added, the solution filtered, concentrated in vacuo to 50 ml and neutralized to pH 7.5. The solid was collected, washed and dried to give the title compound (1.48 g) as a white solid mp 305–7° C.

f) 8-Isopropyl-3-(4-picolyl)-6-thioxantine 1.19 g of 8-isopropyl-3-(4-picolyl)-xanthine and 1.07 g of phosphorus pentasulfide were heated under reflux in 25 ml of pyridine for 4 hours. After cooling to 5° C., 5.28 ml (10.6 mM) of 2N NaOH were added. The solid was filtered off and washed with pyridine. The filtrate was evaporated to dryness, the residue suspended in water and the solid collected, redissolved in 40 ml of 1N NaOH, treated with 0.2 g of charcoal, filtered and neutralized to pH 7.5. The solid was collected, washed and dried to give the title compound (0.99 g) as a white solid mp 310–14° C. (decomposition);

Elemental analysis for $C_{14}H_{15}N_5OS$+0.89% $H_2O$ w/w; % calc.: C 55.29, H 5.07, N 23.03, O 6.05%; % found: C 55.38, H 5.03, N 23.11, O 6.10%.

EXAMPLE 4

3-(3-Chlorobenzyl)-8-isopropyl-6-thioxanthine a) (3-Chlorobenzyl)urea 3.22 g of sodium cyanate was added to a solution of 5.50 ml of 3-chlorobenzylamine in 40 ml of water and 40 ml of THF followed by dropwise addition of 48.6 ml of 1N HCl. After 3 days, the mixture was evaporated to dryness, the residue extracted with hot THF and the filtrate again evaporated to dryness. The residue was suspended in 180 ml of diethyl ether and the solid collected to give the title compound (7.91 g) as a white solid.

b) 1-(3-Chlorobenzyl)-3-cyanoacetyl-urea 3.76 g of 98% cyanoacetic acid and 14 ml of acetic anhydride were heated for 1 hour at 65° C. A solution of 7.73 g of (3-chlorobenzyl)urea in 55 ml THF was added and the mixture kept for 4 hours at 65° C. The THF was removed in vacuo and the residue diluted with 50 ml of toluene. The solid was collected and washed to give the title compound (8.94 g) as a white solid.

c) 6-Amino-1-(3-chlorobenzyl)-uracil

A suspension of 10.17 g (40.4 mM) of 1-(3-chlorobenzyl)-3-cyanoacetyl-urea in 80 ml of 2-propanol was added to a solution of 5.7 g KOH in 40 ml of 2-propanol and heated under reflux for 1 hour. After cooling the solid was collected and washed to give the crude title compound (9.07 g) as an off-white solid.

d) 6-Amino-1-(3-chlorobenzyl)-5-nitroso-uracil 6.4 ml of 4N sodium nitrite was added at 65–70° C. to a suspension of 6.29 g (25 mM) of 6-amino-1-(3-chlorobenzyl)-uracil in 92 ml of acetic acid. After 30 minutes the mixture was cooled, the solid collected and washed with the acetic acid and water to give the title compound (5.21 g) as a pink solid.

e) 6-Amino-1-(3-chlorobenzyl)-5-isobutyrylamino-uracil 4.09 g of 6-amino-1-(3-chlorobenzyl)-5-nitroso-uracil were dissolved in 45 ml of DMF, treated with 2.54 g of sodium carbonate and 0.88 g of neutral Raney-nickel and hydrogenated for 36 hours Isobutyric anhydride (3.6 ml) was added and the mixture shaken for 2 hours at 50° C. The Raney-nickel was filtered off, the filtrate evaporated to dryness, the residue suspended in 100 ml of water and the pH adjusted to 8. The solid was collected, washed and dried to give the crude title compound (4.71 g) as an off-white solid.

f) 3-(3-Chlorobenzyl)-8-isopropyl-xanthine 4.70 g of the 6-amino-1-chlorobenzyl)-5-isobutyrylamino-uracil were heated under reflux in 50 ml 1N NaOH for 30 minutes. The solution was treated twice with 0.3 g of charcoal, filtered and the filtrate adjusted to pH 7.5. The solid was collected, washed and dried to give the title compound (3.52 g) as a white solid mp 319–21° C.

g) 3-(3-Chlorobenzyl)-8-isopropyl-6-thioxanthine 3.19 g of 3-(3-chlorobenzyl)-8-isopropyl-xanthine and 2.67 g of phosphorus pentasulfide were heated under reflux in 35 ml of pyridine for 5 hours. After cooling to −5° C., 13.2 ml (26.4 mM) of 2N NaOH were added over 15 minutes. The reaction mixture was evaporated to dryness, the residue suspended in water, the pH adjusted to 7.5 and the solid collected. The product was redissolved in 100 ml of 1N NaOH, treated with charcoal (5%), filtered and neutralized to pH 7.5. The solid was collected, washed and dried to give 2.29 g of crude thioxanthine. The product was dissolved in 250 ml of chloroform and filtered through 15 g of silica gel. The collected material was reprecipitated from NaOH by neutralization with HCl to give the title compound (2.38 g) as an off-white solid mp 218–20° C.

Elemental analysis for $C_{15}H_{15}ClN_4OS$; % calc.: C 53.81, H 4.52, N 16.73%; % found: C 53.74, H 4.52, N 16.64%.

EXAMPLE 5

3-(4-Chlorobenzyl)-$N^6$-ethyl-8-isopropyl-isoguanine a) 3-(4-Chlorobenzyl)-8-isopropyl-6-thioxanthine 12.75 g of 3-(4-chlorobenzyl)-8-isopropyl-xanthine and 10.67 g of phosphorus pentasulfide were heated under reflux in 200 ml of pyridine for 5.5 hours. After cooling to −5° C., 52.5 ml of 2N NaOH was added over 15 minutes. The solid was filtered off and the filtrate evaporated in vacuo to dryness. The residue was suspended in 250 ml of water (pH 7), the solid collected and washed. The crude product was redissolved in 200 ml of 2N NaOH, treated with 1.4 g of charcoal, filtered and neutralized with 38 ml of 5N HCl to pH 7. The solid was collected, washed and dried to give the crude title compound (12.36 g). This was dissolved in chloroform and filtered through 60 g of silica gel, thereby affording the title compound (10.89 g) as an off-white solid mp 235–6° C. (from acetone).

Elemental analysis for $C_{15}H_{15}ClN_4OS$; % calc.: C 53.81, H 4.52, N 16.73, O 4.78; % found: C 53.79, H 4.47, N 16.74, O 4.77.

b) 3-(4-Chlorobenzyl)-$N^6$-ethyl-8-isopropyl-isoguanine 5.02 g of 3-(4-chlorobenzyl)-8-isopropyl-6-thioxanthine and 60 ml of 70% ethylamine in water was heated in a 450 ml reactor to 150° C.: the pressure rose to 270 psi. After 20 hours the reaction mixture was cooled, filtered and evaporated to dryness. The residue was taken up in water, acidified with 2N HCl to pH 2, and neutralized with 2N NaOH to pH 7. The solid was collected, washed, redissolved in a mixture of 20 ml of methanol, 20 ml of THF and 100 ml of 2N NaOH, treated with 0.5 g of charcoal and filtered. Methanol and THF were removed in vacuo, and the solution neutralized to pH 7 with 5N HCl. The amorphous solid was collected, washed and dried to give the crude product (5.70 g). Recrystallization from methanol gave the title compound (4.42 g) as an off-white solid mp 187–196° C.;

Elemental analysis for $C_{17}H_{20}ClN_9O$ with 1.4% methanol and 1.5% of HCl; % calc.: C 57.85, H 5.88, N 19.67, O 5.27; % found: C 57.61, H 5.75, N 19.67, O 5.27.

EXAMPLE 6

3-Cyclopropylmethyl-8-isopropyl-$N^6$-propyl-isoguanine 5.29 g of 3-cyclopropylmethyl-8-isopropyl-6-thioxanthine and 50 ml of propylamine were heated in a 450 ml reactor to 150° C. After 10 hours, the solution was evaporated to dryness, the residue dissolved in 200 ml of methanol, treated with 0.26 g of charcoal, filtered and concentrated. The crystals were collected, washed and dried to give the title compound (4.81 g) as off-white crystals mp 208–10° C.

Elemental analysis for $C_{15}H_{23}N_5O$; % calc.: C 62.26, H 8.01, N 24.20; % found: C 62.34, H 8.06, N 23.89.

EXAMPLE 7

The hydrochloride salt was also obtained as an off-white solid mp 170–202° C.

8-Cyclopropyl-3, $N^6$-diethyl-isoguanine 5.91 g of 8-cyclopropyl-3-ethyl-6-thioxanthine and 100 ml of 70% ethylamine in water were heated in a 450 ml reactor to 150° C. After 6 hours the solution was filtered and evaporated to dryness. The residue was suspended in methanol, collected, washed and dried to give the title compound (5.67 g) as an off-white solid mp 260° subl./

301–5° C. The hydrochloride salt was also obtained as an off-white solid mp 205–50° C.

Using methods similar to those set out above the following compounds were also prepared:

EXAMPLE 8

8-(3-cyclopentyloxy-4-methoxybenzyl)-3-ethyl-6-thio-xanthine as an off-white solid, mp 195–7° C.

EXAMPLE 9

8-(3,4-dimethoxybenzyl)-3-propyl-6-thio-xanthine as an off-white solid, mp 237–9° C.

EXAMPLE 10

8-(2-naphthylmethyl)-3-propyl-6-thio-xanthine as an off-white solid, mp 220–3° C.

EXAMPLE 11

3-(3-Chlorophenyl)-8-isopropyl-6-thioxanthine 3.66 g (12 mM) of xanthine and 3.20 g (14.4 mM) of phosphorus pentasulfide were refluxed in 57 ml of pyridine for 4 hours. While maintaining the temperature below 10° C., 15.8 ml of 2N NaOH was added slowly with stirring. The solid was filtered off and washed with pyridine. The filtrate was evaporated to dryness and the residue suspended in 100 ml of water. The solid was collected, dissolved in 50 ml of 2N NaOH, treated with 3.80 g of charcoal, filtered and acidified with 5N HCl to pH 6.5. The solid was collected and washed with water: 3.43 g (89.1%) of crude thioxanthine, which was recrystallized twice from methanol: 2.41 g (62.6%) of thioxanthine with mp 290–3° C.

Elemental analysis for $C_{21}H_{13}ClN_4OS$; % calc. C 52.42, H 4.08, N 17.46, O 4.99; % found C 52.61, H 4.05, N 17.49, O 5.02.

EXAMPLE 12

3-(3-Cyclopentyloxy-4-methoxy-benzyl)-$N^6$-ethyl-8-isopropyl-isoguanine 1.20 g (3 mM) of xanthine was refluxed in 12 ml of phosphorus oxychloride for 30 minutes. The excess of oxychloride was removed in vacuo and repeated twice with toluene. The residue was dissolved in 20 ml of THF and treated with 12 ml (150 mM) of aqueous 70% ethylamine with cooling. The two phase mixture was stirred for 60 hours at room temperature and evaporated in vacuo to dryness. The residue was taken up into water/ether and the ether phase washed with 1N NaOH and evaporated. The residue (0.95 g) was chromatographed on 9 g of silica gel with chloroform. Fractions 6 to 13 were combined (0.57 g) and crystallized from aqueous ether: 0.28 g (21.0%) of isoguanine with mp 110–5° C.

Elemental analysis for $C_{23}H_{31}N_5O_3$—$H_2O$; % calc. C 62.28, H 7.50, N 15.79, O 14.43; % found C 61.98, H 7.53, H 15.55, O 14.69.

EXAMPLE 13

Protocols for PDE IV, PDE III and PDE V inhibition activity are set forth below:

Type III Phosphodiesterase Enzyme Isolation Protocol

The Type III PDE is isolated from human platelets using a procedure similar to that previously described by Weishaar, R. E. et al., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM $Na_2$ EDTA). The proteinase inhibitor phenylmethyl-sulfonyl fluoride (PMSF) is also included in this buffer at a final concentration of 200 $\mu$M. The suspension is homogenized using a polytron and the homogenate centrifuged at 100,000×g for 60 minutes. This and all subsequent procedures are performed at 0–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 $\mu$M PMSF). After application of the sample, the column is washed with several bed volumes of buffer B, after which the different forms of PDE are eluted from the column using two successive linear NaCl gradients (0.05–0.15 M, 300 ml total; 0.15–0.40 Ma 200 ml total); Five ml fractions are collected and assayed for cyclic AMP and cyclic GMP PDE activity., Fractions containing PDE III activity are pooled and dialyzed overnight against 4 L of buffer B. The dialyzed PDE III is then concentrated to 10% of the original volume, diluted to 50% with ethylene glycol monoethyl ether and stored at -20° C. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 $\mu$M, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase Enzyme Isolation Protocol

The Type IV PDE is isolated from bovine tracheal smooth muscle using a procedure similar to that previously described by Silver, P. J. et al., Eur. J. Pharmacol. 150:85, 1988. Briefly, smooth muscle from bovine trachea is minced and homogenized using a polytron in 10 volumes of an extraction buffer containing 10 mm Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at -20° C.

Measuring Type IV PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 µM, which approximates the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type V Phosphodiesterase Enzyme Isolation Protocol

Enzyme Isolation Procedure:

The Type V PDE is isolated using a procedure similar to that previously described by Weishaar et al., Hypertension 15:528, (1990). Briefly, 1–2 units of platelets are suspended in an equal volume of buffer A (20 mM Tris-HCl, pH 7.5, containing 2 mM magnesium acetate, 1 mM dithiothreitol, and 5 mM $Na_2EDTA$) using a polytron. The proteinase inhibitor phenylmethylsulfonyl fluoride (PMSF) are also included in this buffer at a final concentration of 200 uM. This and all subsequent procedures are performed at 0–4° C. The homogenate is then centrifuges at 100,000×g for 60 minutes. The supernatant is then removed and filtered through four layers of gauze and applied to a DEAE-Trisacryl M column. The column is washed with several bed volumes of buffer B (20 mM Tris-HCl, pH 7.5, containing 2 mM magnesium acetate, 1 mM diothiothreitol, and 200 uM PMSF) and eluted by two successive linear NaCl gradients (0.05–0.15 M, 300 ml total; 0.15–0.40 M, 200 ml total). Five ml fractions are collected and assayed for cyclic AMP and cyclic GMP PDE activity. Fractions that contain PDE V are pooled and dialyzed overnight against 4 L of buffer C (20 mm Tris-HCl, pH 7.5, containing 2 mM magnesium acetate and proteinase inhibitors). The dialyzed PDE V is then concentrated to 10% of the original volume, diluted to 50% with ethylene glycol monoethyl ether and stored at –20° C. PDE V can typically be retained for up to four weeks with little or no loss of activity.

Measuring Type V PDE Activity

Enzyme activity are assessed by measuring the hydrolysis of [$^3$H]-cyclic GAP, as described by Thompson et al. (Thompson, W. J., Teraski, W. L., Epstein, P. N., Strada, S. J.: Adv. Cyclic Nucleotide Res. 10:69, 1979). The cyclic GMP concentration used in this assay is 0.2 uM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%. The reference Type V PDE inhibitor zaprinast is evaluated with each assay.

The compounds are tested over concentration range: 0.1, 1, 10, 100 uM (n=1), and $IC_{50}$ determinations are made using 5 appropriate concentrations (n=2).

EXAMPLE 14

Following the above procedures, the PDE III, PDE IV and PDE V inhibition $IC_{50}$'s for several of the compounds of the above Examples and rolipram were tested and compared. The results are shown in Table 1 below:

TABLE 1

PDE ACTIVITY

| Compound | PDE IV | PDE III | PDE V |
|---|---|---|---|
| Ex. 1 | 1.0 | 25 | 25.7 |
| Ex. 2 | 78 | 25 | — |
| Ex. 3 | 18.2 | 215 | — |
| Ex. 4 | 4.1 | 44 | 0.7 |
| Ex. 5a | 8.6 | 29 | 2.0 |
| Ex. 5b | 9.4 | 317 | 0.5 |
| Ex. 6 | 24 | 492 | — |
| Ex. 7 | 51 | 207 | — |
| Ex. 8 | 4.0 | 28.2 | 23.9 |
| Ex. 9 | 8.5 | 23.6 | — |
| Ex. 10 | 2.8 | 2.7 | 3.8 |
| Ex. 11 | 22.40 | 311 | 65.4 |
| Rolipram | 2.6 | 790 | 500 |

$IC_{50}$ (µM)

As can be seen from the foregoing, the inventive compounds provide high levels of PDE IV inhibition while at the same time relatively low levels of PDE III inhibition. Thus, the inventive compounds provide selectivity with regard to PDE IV inhibition.

While the invention has been illustrated with respect to the production and use of a particular compound, it is apparent that variations and modifications of the invention can be made without departing from the spirit or scope of the invention.

What is claimed is:

1. A compound of formula II:

(II)

wherein:

$Q_3$, $Q_{6a}$, $Q_{6b}$, and $Q_8$ are independently a bond, $C_{1-8}$ alkylene, $C_{2-8}$ alkenylene and $C_{2-8}$ alkynylene, and $R_3$, $R_{6a}$, $R_{6b}$, and $R_8$ are independently hydrogen, aryl, or heteroaryl, which is optionally substituted by halogen, hydroxy, alkoxy, nitro, cyano and carboxy, provided that $Q_3R_3$ is not hydrogen or methyl; and pharmaceutically acceptable salts thereof.

2. The compound of claim 1, wherein one of said $C_{1-8}$ alkylene, $C_{2-8}$ alkenylene and $C_{2-8}$ alkynylene is branched.

3. The compound of claim 1, wherein one of said $C_{1-8}$ alkylene, $C_{2-8}$ alkenylene and $C_{2-8}$ alkynylene is unbranched.

4. The compound of claim 1, wherein one of said $C_{1-8}$ alkylene, $C_{2-8}$ alkenylene and $C_{2-8}$ alkynylene is further substituted with one or more halogens, hydroxy or alkoxy groups, or cycloalkyl groups.

5. The compound of claim 1, wherein one of $R_3$, $R_{6a}$, $R_{6b}$, and $R_8$ is an aryl selected from the group consisting of phenyl and naphthyl.

6. The compound of claim 1, wherein one of $R_3$, $R_{6a}$, $R_{6b}$, and $R_8$ is a heteroaryl selected from the group consisting of pyridyl, pyrimidyl, quinolyl and isoquinolyl.

7. A compound of claim 1 selected from the group consisting of:

3-(4-chlorobenzyl)-N⁶-ethyl-8-isopropyl-isoguanine;
3-(cyclopropylmethyl)-8-(1-methyl-ethyl)-N⁶-propyl-isoguanine hydrochloride;
8-cyclopropyl-3, N⁶-diethyl-isoguanine hydrochloride;
3-(3-Cyclopentyloxy-4-methoxy-benzyl)-N⁶-ethyl-8-isopropyl-isoguanine; and
pharmaceutically acceptable salts thereof.

8. The compound of claim 1, wherein $Q_8$ is $C_{1-8}$ alkylene, $C_{2-8}$ alkenylene and $C_{2-8}$ alkynylene.

9. A method of treating a mammal suffering from a disease state selected from the group consisting of asthma, allergies, depression and rhinitis, comprising administering an effective amount of the compound of formula (II):

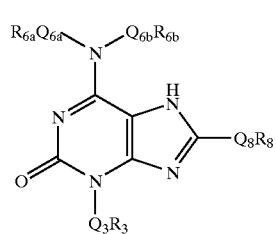

(II)

wherein:

$Q_3$, $Q_{6a}$, $Q_{6b}$, and $Q_8$ are independently a bond, $C_{1-8}$ alkylene, $C_{2-8}$ alkenylene and $C_{2-8}$ alkynylene, and $R_3$, $R_{6a}$, $R_{6b}$, and $R_8$ are independently hydrogen, aryl, or heteroaryl, which is optionally substituted by halogen, hydroxy, alkoxy, nitro, cyano and carboxy, provided that $Q_3R_3$ is not hydrogen or methyl; and pharmaceutically acceptable salts thereof.

10. A method of effecting PDE IV inhibition to a patient requiring the same, which comprises administering an effective amount of the compound of claim 1 in a patient in need thereof.

11. The method of claim 10, wherein said compound is selected from the group consisting of:
3-(4-chlorobenzyl)-N⁶-ethyl-8-isopropyl-isoguanine;
3-(cyclopropylmethyl)-8-(1-methyl-ethyl)-N⁶-propyl-isoguanine hydrochloride;
8-cyclopropyl-3, N⁶-diethyl-isoguanine hydrochloride;
3-(3-Cyclopentyloxy-4-methoxy-benzyl)-N⁶-ethyl-8-isopropyl-isoguanine; and
pharmaceutically acceptable salts thereof.

12. The method of claim 9, wherein $Q_8$ is $C_{1-8}$ alkylene, $C_{2-8}$ alkenylene and $C_{2-8}$ alkynylene.

13. The method of claim 9, wherein said compound is selected from the group consisting of
3-(4-chlorobenzyl)-N⁶-ethyl-8-isopropyl-isoguanine;
3-(cyclopropylmethyl)-8-(1-methyl-ethyl)-N⁶-propyl-isoguanine hydrochloride;
8-cyclopropyl-3, N⁶-diethyl-isoguanine hydrochloride;
3-(3-Cyclopentyloxy-4-methoxy-benzyl)-N⁶-ethyl-8-isopropyl-isoguanine; and
pharmaceutically acceptable salts thereof.

14. A pharmaceutical composition comprising a pharmaceutically acceptable carrier and the compound of formula (II):

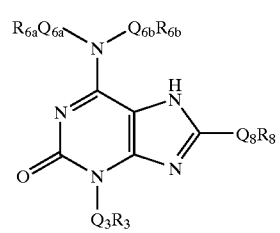

(II)

wherein:

$Q_3$, $Q_{6a}$, $Q_{6b}$, and $Q_8$ are independently a bond, $C_{1-8}$ alkylene, $C_{2-8}$ alkenylene and $C_{2-8}$ alkynylene, and $R_3$, $R_{6a}$, $R_{6b}$, and $R_8$ are independently hydrogen, aryl, or heteroaryl, which is optionally substituted by halogen, hydroxy, alkoxy, nitro, cyano and carboxy, provided that $Q_3R_3$ is not hydrogen or methyl; and pharmaceutically acceptable salts thereof.

15. The pharmaceutical composition of claim 14, wherein said compound is selected from the group consisting of
3-(4-chlorobenzyl)-N⁶-ethyl-8-isopropyl-isoguanine;
3-(cyclopropylmethyl)-8-(1-methyl-ethyl)-N⁶-propyl-isoguanine hydrochloride;
8-cyclopropyl-3, N⁶-diethyl-isoguanine hydrochloride;
3-(3-Cyclopentyloxy-4-methoxy-benzyl)-N⁶-ethyl-8-isopropyl-isoguanine; and
pharmaceutically acceptable salts thereof.

16. The pharmaceutical composition of claim 14, wherein $Q_8$ is $C_{1-8}$ alkylene, $C_{2-8}$ alkenylene and $C_{2-8}$ alkynylene.

* * * * *